United States Patent
Bischoff et al.

(10) Patent No.: US 7,224,471 B2
(45) Date of Patent: May 29, 2007

(54) AZIMUTHAL SCANNING OF A STRUCTURE FORMED ON A SEMICONDUCTOR WAFER

(75) Inventors: Joerg Bischoff, Illmenau (DE); Shifang Li, Pleasanton, CA (US); Xinhui Niu, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 99 days.

(21) Appl. No.: 10/696,246

(22) Filed: Oct. 28, 2003

(65) Prior Publication Data

US 2005/0088665 A1    Apr. 28, 2005

(51) Int. Cl.
G01B 11/24    (2006.01)
G01J 4/00    (2006.01)

(52) U.S. Cl. .................. 356/601; 356/364; 356/367

(58) Field of Classification Search .. 356/237.1–237.5, 356/629–630, 364–369, 601–625; 250/559.01, 250/559.09, 559.16, 492.2, 492.22; 73/800
See application file for complete search history.

(56) References Cited

U.S. PATENT DOCUMENTS

| | | | | |
|---|---|---|---|---|
| 4,516,159 A | * | 5/1985 | Diepeveen | 358/494 |
| 4,606,645 A | * | 8/1986 | Matthews et al. | 356/446 |
| 4,672,196 A | * | 6/1987 | Canino | 250/225 |
| 4,837,603 A | * | 6/1989 | Hayashi | 356/369 |
| 4,898,471 A | * | 2/1990 | Vaught et al. | 356/394 |
| 5,042,951 A | * | 8/1991 | Gold et al. | 356/369 |
| 5,076,692 A | * | 12/1991 | Neukermans et al. | 356/338 |
| 5,432,607 A | * | 7/1995 | Taubenblatt | 356/364 |
| 5,883,710 A | * | 3/1999 | Nikoonahad et al. | 356/237.2 |
| 5,979,244 A | * | 11/1999 | Michaelis | 73/800 |
| 6,020,957 A | * | 2/2000 | Rosengaus et al. | 356/237.4 |
| 6,031,614 A | * | 2/2000 | Michaelis et al. | 356/369 |
| 6,323,947 B1 | * | 11/2001 | Freeouf | 356/369 |
| 6,448,097 B1 | * | 9/2002 | Singh et al. | 438/16 |
| 6,486,946 B1 | * | 11/2002 | Stover et al. | 356/237.2 |
| 6,538,730 B2 | * | 3/2003 | Vaez-Iravani et al. | 356/237.2 |
| 6,609,086 B1 | * | 8/2003 | Bao et al. | 702/189 |
| 6,785,638 B2 | | 8/2004 | Niu et al. | |
| 6,816,249 B2 | * | 11/2004 | Fairley et al. | 356/237.1 |
| 6,819,426 B2 | * | 11/2004 | Sezginer et al. | 356/401 |
| 6,891,626 B2 | | 5/2005 | Niu et al. | |
| 6,943,900 B2 | | 9/2005 | Niu et al. | |
| 2004/0267397 A1 | | 12/2004 | Doddi | |

* cited by examiner

*Primary Examiner*—Sang H. Nguyen
(74) *Attorney, Agent, or Firm*—Morrison & Foerster LLP

(57) ABSTRACT

A structure formed on a semiconductor wafer is examined by directing an incident beam at the structure at an incidence angle and a azimuth angle. The incident beam is scanned over a range of azimuth angles to obtain an azimuthal scan. The cross polarization components of diffracted beams are measured during the azimuthal scan.

23 Claims, 6 Drawing Sheets

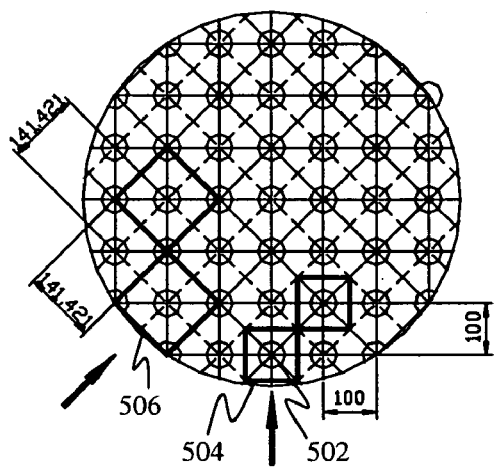
Fig. 5-A
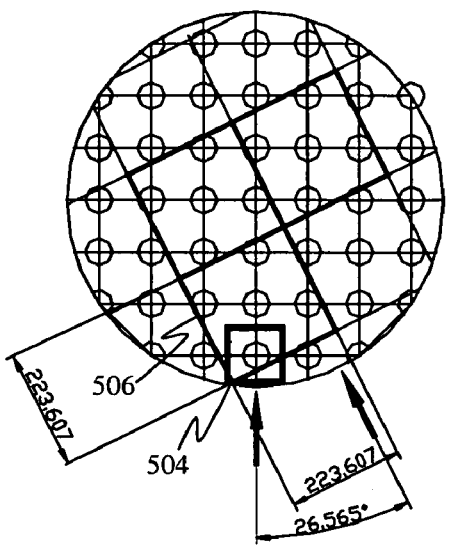
Fig. 5-B
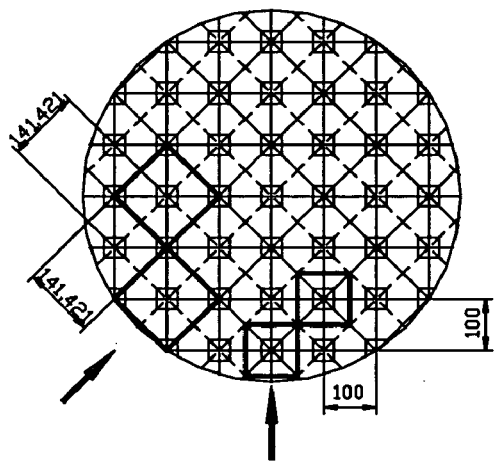
Fig. 5-C
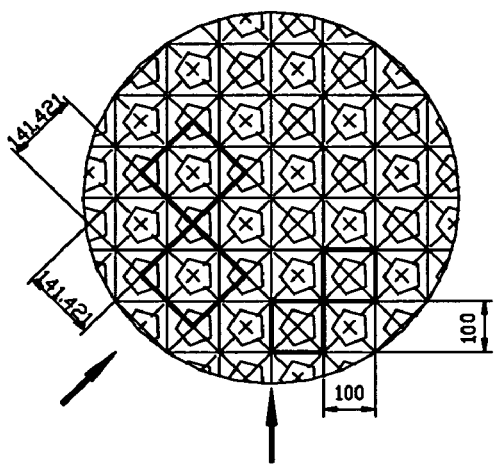
Fig. 5-D

AZIMUTHAL SCANNING OF A STRUCTURE FORMED ON A SEMICONDUCTOR WAFER

BACKGROUND

1. Field of the Invention

The present application relates to optical metrology, and more particularly to azimuthal scanning of a structure formed on a semiconductor wafer.

2. Related Art

Optical metrology involves directing an incident beam at a structure, measuring the resulting diffracted beam, and analyzing the diffracted beam to determine a feature of the structure. In semiconductor manufacturing, optical metrology is typically used for quality assurance. For example, after fabricating a grating array in proximity to a semiconductor chip on a semiconductor wafer, an optical metrology system is used to determine the profile of the grating array. By determining the profile of the grating array, the quality of the fabrication process utilized to form the grating array, and by extension the semiconductor chip proximate the grating array, can be evaluated.

However, when performing optical metrology on a structure, measurement errors may occur if the structure and the incident beam are not properly aligned azimuthally. In particular, cross polarization components of the diffracted beam may complicate the signal measurements, and cause mis-fitting between the measured signals and the analysis model used in optical metrology.

Additionally, optical metrology of three dimensional (3-D) structures, e.g., grating arrays with a dimensionality in two directions, such as contact hole arrays, are increasingly being used in the semiconductor industry. Due to the additional dimension compared to two dimensional (2-D) structures, such as lines/spaces, performing optical metrology of 3-D structures is more complex. For example, in optical metrology of 2-D structure, the critical dimension (CD) in one lateral direction is primarily of interest. In contrast, in optical metrology of 3-D structures, besides the CD, the shape (from a bird's view), the CD ratio, and the orientation of the structures are of interest.

SUMMARY

In one exemplary embodiment, a three dimensional (3-D) structure formed on a semiconductor wafer is examined by directing an incident beam at the 3-D structure at an incidence angle and a azimuth angle. The incident beam is scanned over a range of azimuth angles to obtain an azimuthal scan. The cross polarization components of diffracted beams are measured during the azimuthal scan.

DESCRIPTION OF DRAWING FIGURES

The present invention can be best understood by reference to the following description taken in conjunction with the accompanying drawing figures, in which like parts may be referred to by like numerals:

Figure 6:
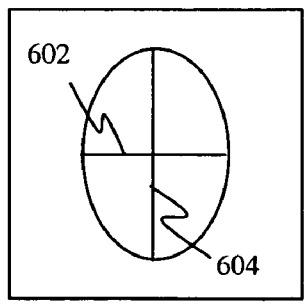
Figure 7:
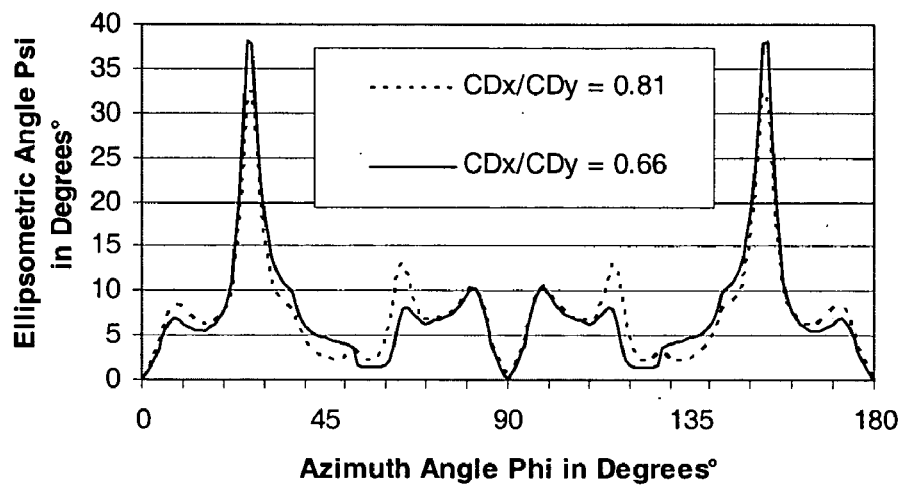
Figure 8:
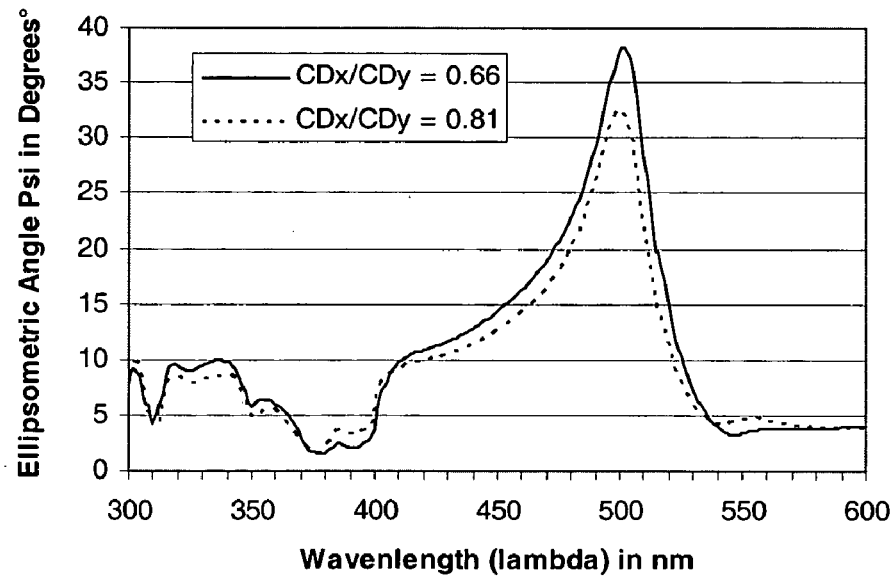
Figure 9:
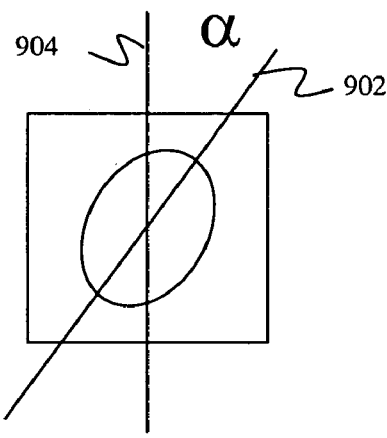
Figure 10:
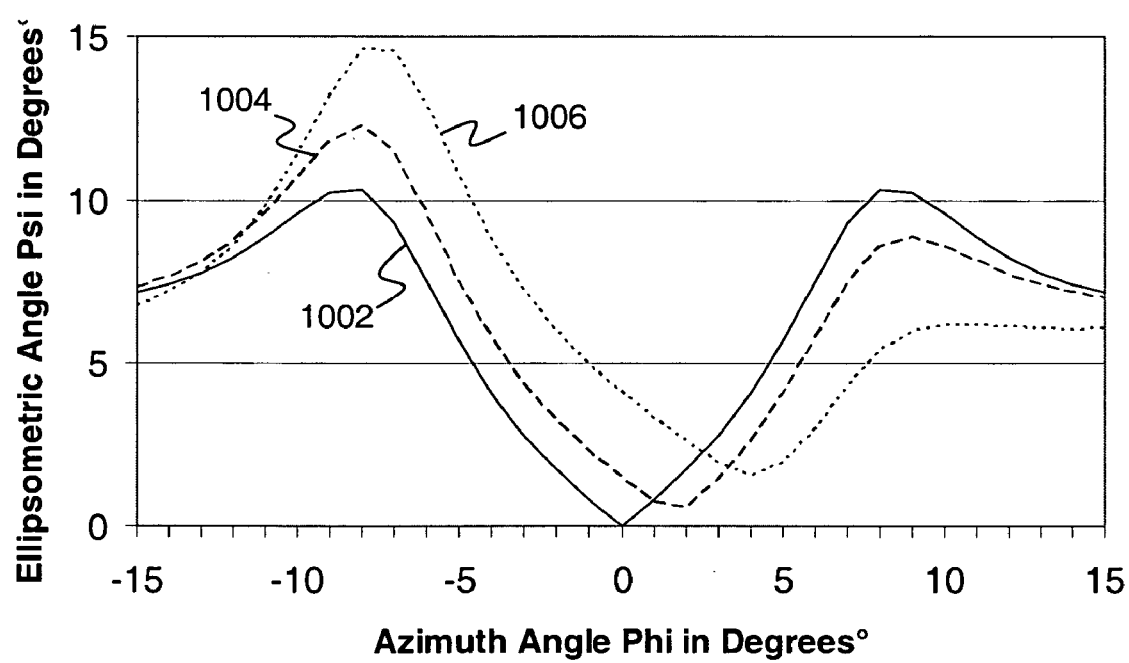
Figure 11:
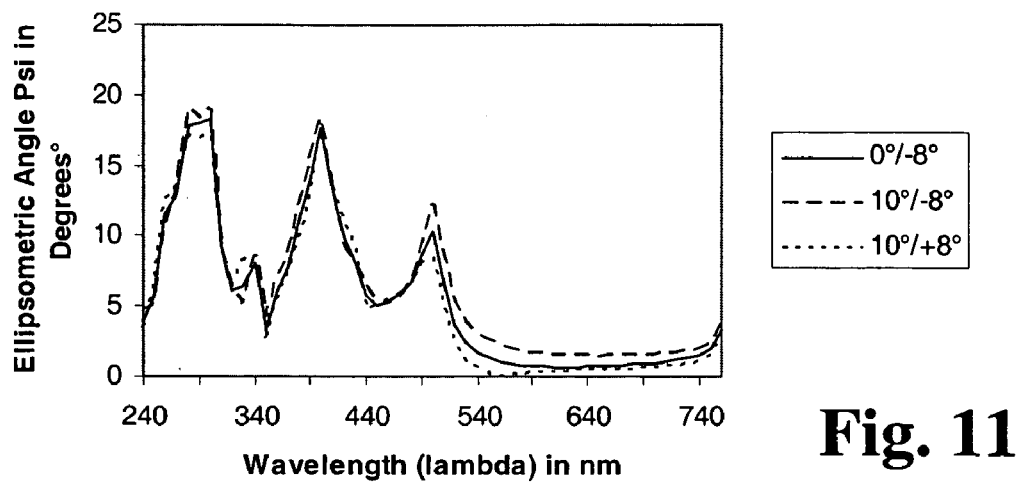
Figure 12:
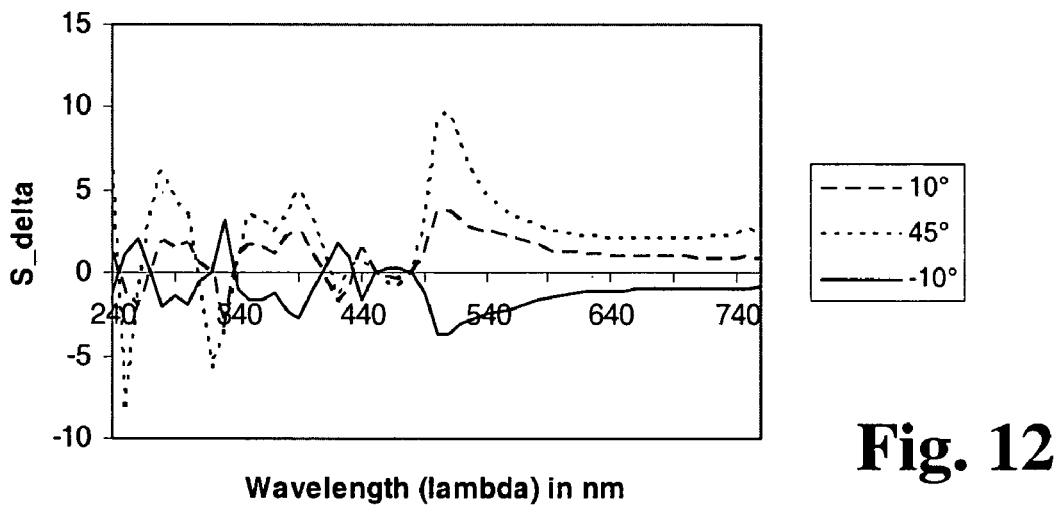

FIGS. 5-A to 5-D depict exemplary grating arrays;

FIG. 6 depicts a portion of another exemplary grating array;

FIG. 7 depicts the results of another exemplary simulation of signal measurements from the exemplary grating array depicted in FIG. 6;

FIG. 8 depicts the results of an exemplary simulation of a spectral scan from the exemplary grating array depicted in FIG. 6;

FIG. 9 depicts a portion of another exemplary grating array;

FIG. 10 depicts the results of another exemplary simulation of signal measurements from the exemplary grating array depicted in FIG. 9;

FIG. 11 depicts a spectral scan the exemplary grating array depicted in FIG. 9;

FIG. 12 depicts a spectral scan of a difference signal; and

Figure 13:
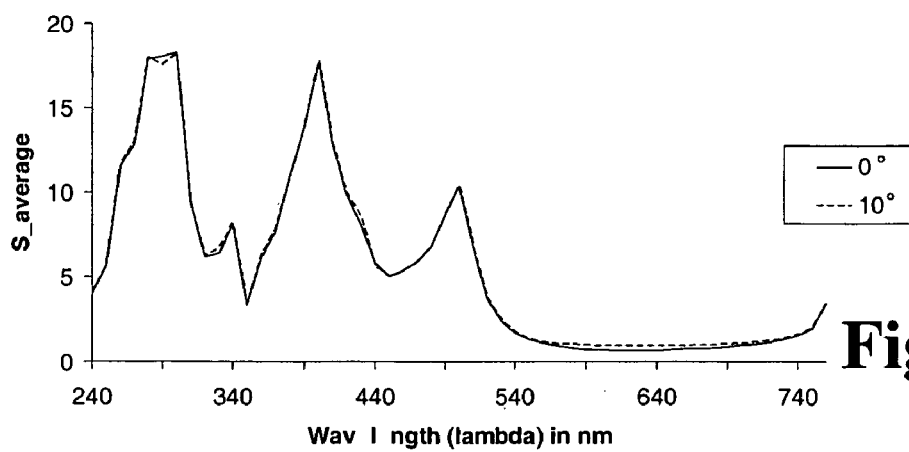

FIG. 13 depicts a spectral scan of an average signal.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology

Figure 1:
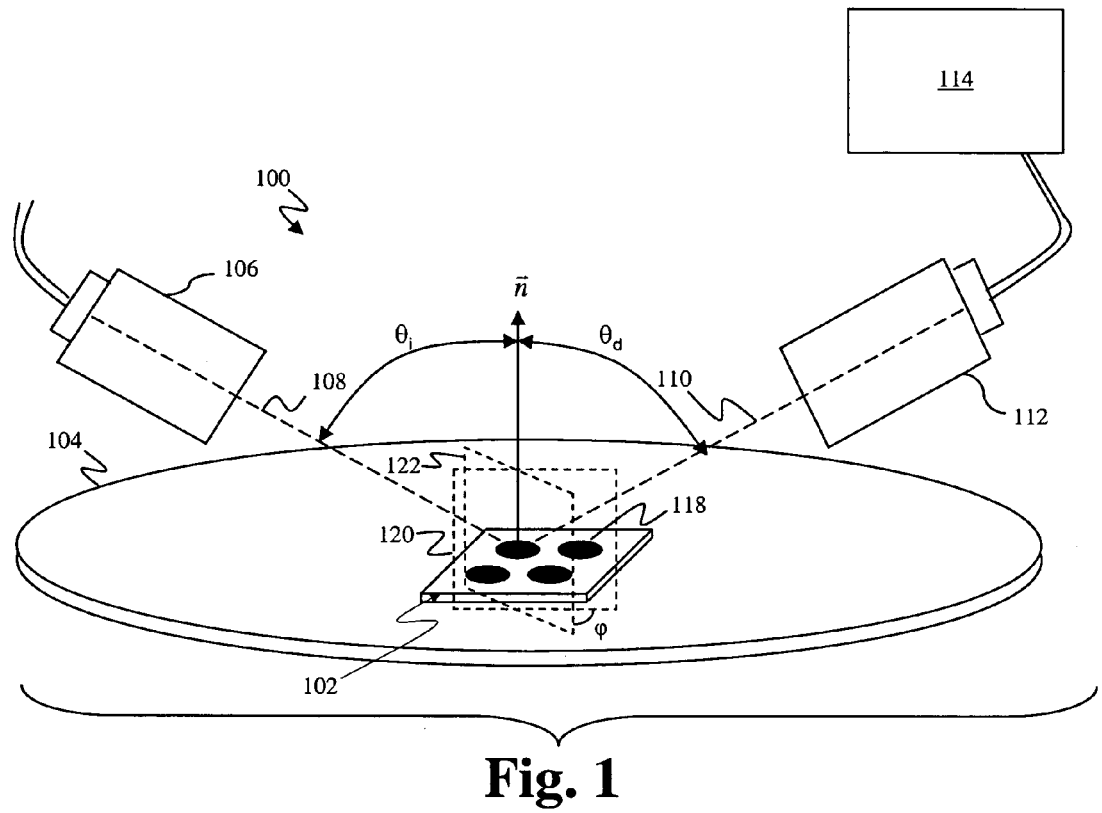
FIG. 1 depicts an exemplary optical metrology system.

With reference to FIG. 1, an optical metrology system 100 can be used to examine and analyze a 3-D structure formed on a semiconductor wafer. For example, optical metrology system 100 can be used to determine a feature of a grating array 102 formed on wafer 104. As described earlier, grating array 102 can be formed in test areas on wafer 104, such as adjacent to a device formed on wafer 104. Alternatively, grating array 102 can be formed in an area of the device that does not interfere with the operation of the device or along scribe lines on wafer 104. Although grating array 102 is depicted in FIG. 1 as a contact hole array, it should be recognized that grating array 102 can include various 2-D and 3-D structures.

As depicted in FIG. 1, optical metrology system 100 can include an optical metrology device with a source 106 and a detector 112. Grating array 102 is illuminated by an incident beam 108 from source 106. In the present exemplary embodiment, incident beam 108 is directed onto grating array 102 at an angle of incidence $\theta_i$ with respect to normal $\vec{n}$ of grating array 102 and an azimuth angle $\phi$ (i.e., the angle between the plane of incidence beam 108 (incidence plane 122) and the direction of the periodicity of grating array 102 (grating plane 120)). Diffracted beam 110 leaves at an angle of $\theta_d$ with respect to normal $\vec{n}$ and is received by detector 112. Detector 112 measures the diffracted beam 110 as a measured diffraction signal, which can include reflectance, zero order cross polarization efficiencies/amplitudes, tan ($\Psi$), cos ($\Delta$), Fourier coefficients, and the like.

Optical metrology system 100 also includes a processing module 114 configured to receive the measured diffraction signal and analyze the measured diffraction signal. As described below, a feature of grating array 102 can then be determined using various linear or non-linear profile extraction techniques, such as a library-based process, a regression-based process, and the like. For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety. For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety. For a more detailed description of a machine learning system, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

2. Azimuthal Scanning

Figure 2:
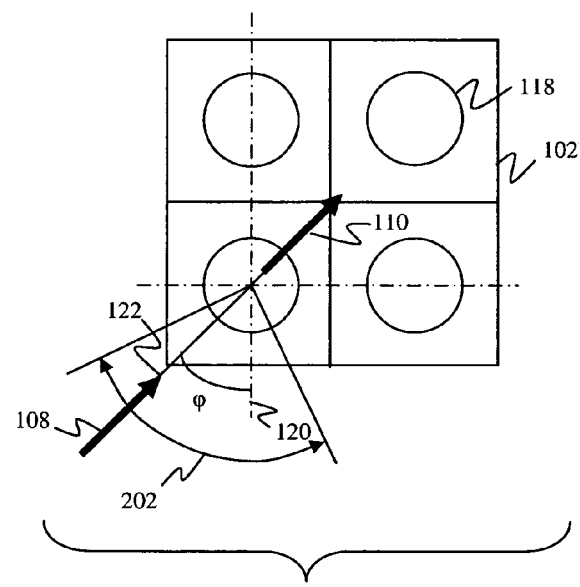
FIG. 2 depicts an exemplary grating array.

With reference to FIG. 1, as described above, incident beam 108 is directed at grating array 102 at an incidence angle of $\theta_i$ and an azimuth angle $\phi$. With reference to FIG. 2, in one exemplary embodiment, an azimuthal scan is performed by scanning incident beam 108 over a range of azimuth angles 202. As incident beam 108 is scanned over the range of azimuth angles 202, measurements of diffracted beam 110 (i.e., signal measurements), in particular the cross polarization terms of diffracted beam 110, are obtained using detector 112. As noted above, the signal measurements can include reflectance, zero order cross polarization efficiencies/amplitudes, tan ($\Psi$), cos ($\Delta$), Fourier coefficients, and the like.

For example, for a typical ellipsometer, detector 112 (FIG. 1) measures the ellipsometer parameters ($\psi$, $\Delta$). Thus, the effective ellipsometer parameter $\tilde{\rho}$ can be express as:

$$\tilde{\rho} = \tan\psi e^{i\Delta} = \frac{E_p}{E_s} = \frac{R_{pp}\mathrm{Sin}P + R_{sp}\mathrm{Cos}P}{R_{ps}\mathrm{Sin}P + R_{ss}\mathrm{Cos}P}$$

where $E_p$ is the electric field parallel to the plane of incidence, $E_s$ is the electric field perpendicular to the plane of incidence, P is the polarization angle, and $R_{pp}$, $R_{sp}$, $R_{ps}$, and $R_{ss}$ are the polarization terms. As the azimuth scan is performed, all four polarization terms $R_{pp}$, $R_{sp}$, $R_{ps}$, and $R_{ss}$ change. The cross-polarization terms, $R_{sp}$, $R_{ps}$, are typically small in quantity relative to the in-polarization terms, $R_{ss}$, $R_{pp}$. Note that when P is in the range of 20–50°, the cross-polarization terms are difficult to measure because the contribution of the cross-polarization terms is not easily distinguished from the contribution of the in-polarization terms. However, when P is 0° or 90°, one of the in-polarization terms, $R_{ss}$ or $R_{pp}$, vanishes, leaving the cross-polarization terms alone either as S or P component of the diffracted beam. Thus, in the present exemplary embodiment, the azimuthal scans are performed using a polarization angle of 0° or 90°.

3. Determining Zero Azimuth Position

Optical metrology typically includes comparing a measured diffraction signal to a simulated diffraction signal, where the simulated diffraction signal is associated with a hypothetical profile of the structure. If the measured diffraction signal matches the simulated diffraction signal or when the difference of the measured diffraction signal and the simulated diffraction signal is within a preset or matching criterion, the hypothetical profile associated with the matching simulated diffraction signal is presumed to represent the actual profile of the structure.

The simulated diffraction signal used in optical metrology are typically generated using a modeling technique, such as rigorous coupled wave analysis (RCWA), integral method, Fresnel method, finite analysis, modal analysis, and the like. For a detailed description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety. The simulated diffraction signal can also be generated using a machine learning system. For a more detailed description of a machine learning system, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In generating the simulated diffraction signal, an azimuth angle is assumed. Differences between the azimuth angle assumed in generating the simulated diffraction signal (i.e., the assumed azimuth angle) and the azimuth angle used in obtaining the measured diffraction signal (i.e, the actual azimuth angle) may produce erroneous results. For example, due to the difference in the assumed and azimuth angles, the hypothetical profile associated with the matching simulated diffraction signal may not be representative of the actual profile.

Thus, in one exemplary application, the signal measurements obtained during an azimuthal scan are used to determine a zero azimuth position, where the cross polarization terms are zero, to detect azimuthal misalignment between the azimuth angle used in obtaining the measured diffraction signal with the azimuth angle used in generating the simulated diffraction signal. As described in more detail below, the signal measurements, and more particularly the cross polarization terms of the signal measurements, are zero at certain azimuth angles.

For example, when using an ellipsometer and a polarization angle P of 0° or 90°, the ellipsometer signal can be express as:

$$\tilde{\rho} = \tan\psi e^{i\Delta} = \frac{E_p}{E_s} = \frac{R_{sp}}{R_{ss}} \text{ or } \tilde{\rho} = \tan\psi e^{i\Delta} = \frac{E_p}{E_s} = \frac{R_{ps}}{R_{pp}}$$

If only the amplitude terms are considered, the angle $\psi$ can be expressed as:

$$\psi = a\tan\frac{|R_{sp}|}{|R_{ss}|} \text{ or } \psi = a\tan\frac{|R_{ps}|}{|R_{pp}|}.$$

The signal measurements, and more particularly the cross polarization terms of the signal measurements, zero when $\phi$ is 0°, 45°, 90°, 135°, 180°, 225°, 270°, and 315°.

Figure 3:
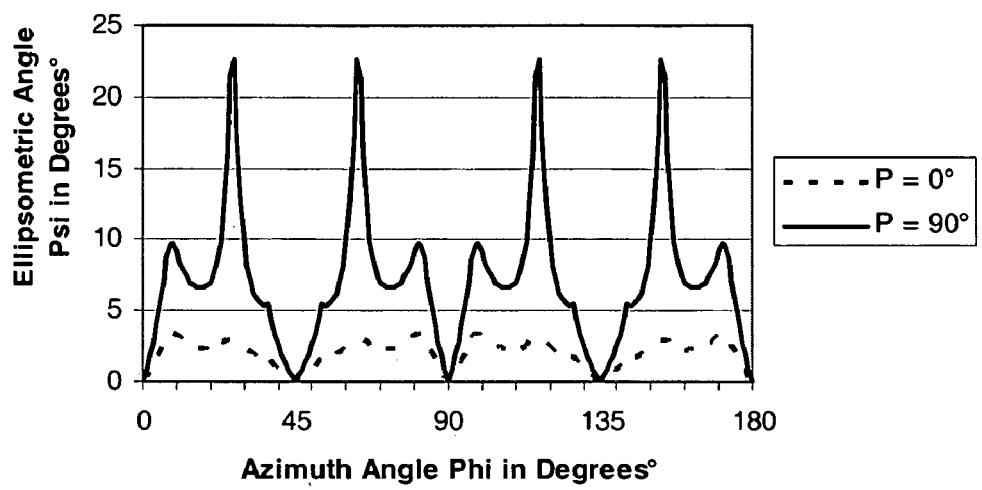
FIG. 3 depicts the results of an exemplary simulation of signal measurements from the exemplary grating array depicted in FIG. 2.

With reference to FIG. 3, the results of a simulation of an azimuthal scan of a contact hole array are depicted. The simulation depicted in FIG. 3 assumed a contact hole array having a photoresist on silicon structure having a pitch x, y of 400 nm, the photoresist having a thickness of 200 nm, the holes having a diameter of 200 nm, an angle of incidence of 65°, and light having a wavelength ($\lambda$) of 500 nm.

FIG. 3 depicts two signal measurements, in this example angle ψ, over a range of φ from 0° to 180°. As depicted in FIG. 3, the signal measurements are for a polarization angle P of 0° and 90° (note that −ψ was plotted for P of 90° in order to allow comparison of the two signal measurements). As also depicted in FIG. 3, the signal measurements are zero at 0°, 45°, 90°, and 135°. Additionally, the signal measurements are symmetric about these zero points. As also depicted in FIG. 3, the signal measurement that corresponds to P of 90° is stronger than the signal measurement that corresponds to P of 0°, and thus would provide a better signal-to-noise ratio (SNR).

Thus, in the present exemplary application, the simulated diffraction signals used in optical metrology of a grating array are generated using an azimuth angle corresponding to when the signal measurements, and more particularly the cross polarization terms of the signal measurement, are zero, such as φ of 0°, 45°, 90°, 135°, 180°, 225°, 270°, or 315°. Before obtaining the measured diffraction signal from a grating array to compare to a simulated diffraction signal, an azimuthal scan of the grating array is performed. The signal measurements obtained from the azimuthal scan can then be used to detect misalignment of the azimuth angle to be used in obtaining the measured diffraction signal. In addition to detecting misalignment of the azimuth angle, the amount of the misalignment can be determined from the signal measurements. The misalignment can then be corrected. For example, if there is an offset between the assumed azimuth angle and the actual azimuth angle (e.g., if the curve is shifted in lateral direction or the zero is shifted, such as from 90° to 91.2°), the azimuthal calibration error of the optical metrology hardware (e.g., of 1.2°) can be detected and corrected.

Figure 4:
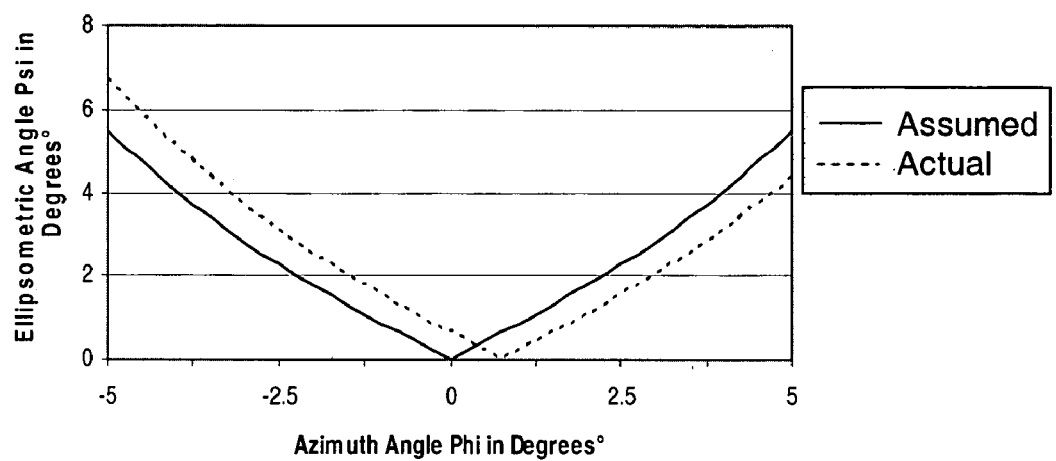
FIG. 4 depicts the results of another exemplary simulation of signal measurements from the exemplary grating array depicted in FIG. 2.

Although FIG. 3 depicts performing the azimuthal scan over a range of 180° degrees, it should be recognized that the azimuthal scan can be performed over any range around the assumed azimuth angle (i.e., the azimuth angle used to generate the simulated diffraction signals). For example, FIG. 4 depicts performing an azimuthal scan over a range of −5° to +5° around the assumed azimuth angle of 0°. As depicted in FIG. 4, the angular offset between the actual and the assumed azimuth angles is about 0.75°.

With reference again to FIG. 2, when the shape of the structures of grating array 102, which in FIG. 2 are holes, is mirror image symmetric about incident plane 122, the cross polarization terms are zero. Additionally, for all equal pitch of the mirror symmetric structure, the cross polarization terms are zero at φ of 45°, 135°, 225°, and 315°.

For example, with reference to FIG. 5-A, a grating array of holes 502 is depicted. At φ of 0°, cells 504 of the grating array have a pitch of 100 nm. Because holes 502 are mirror image symmetric about the incident plane at φ of 0°, the cross, polarization terms are zero. As depicted in FIG. 5-A, at φ of 45°, cells 506 have a pitch of 141.421 nm. Because holes 502 are mirror image symmetric about the incident plane at φ of 45°, the cross polarization terms are still zero. However, because the size of cells 506 and the structure within cells 506 are different than cells 504, the in-polarization terms are different at φ=45° than φ=0°.

More generally, when the shape of the structure of the grating array is mirror image symmetric, the cross polarization terms are zero at φ=tan$^{-1}$(n/m), where n,m=0, ±1, ±2, ±3, etc. The pitch of cell 506 can be determined based on the pitch of cell 504. More particularly the pitch of cell 506 is the pitch of cell 504×sqrt($n^{-2}+m^{-2}$). For example, as depicted in FIG. 5-B, when n=1 and m=2, φ=tan$^{-1}$(0.5) =26.565°. Also, the pitch of cell 504 is 100 nm, so the pitch of cell 506 is 10×sqrt(5)=223.6 nm.

It should be recognized that various shapes can produce the mirror image symmetry described above. For example, FIG. 5-C depicts a square shaped structure, which is mirror image symmetric at both φ=0° and φ=45°. Thus, for the grating array depicted in FIG. 5-C, the cross polarization terms are zero at both φ=0° and φ=45°. FIG. 5-D depicts a shape that is not mirror image symmetric at both φ=0° and φ=45°.

4. Determining CD-Ratio

As described above, in semiconductor manufacturing, optical metrology is typically used for quality assurance. For example, in semiconductor manufacturing, a lithographic process is typically used to transfer patterns from a mask onto a semiconductor wafer to form structures on the wafer. Aberrations in the lithographic process, however, can produce inaccuracies in the patterns transferred to the wafer and thus the structures formed on the wafer. For example, due to lens aberrations, such as astigmatism, circular contact holes on a mask may produce elliptical holes on the wafer.

Thus, in one exemplary application, the signal measurements obtained during an azimuthal scan are used to detect elliptical-shaped contact holes. More particularly, with reference to FIG. 6, the signal measurements can be used to determine a CD ratio. For example, a CD ratio of a first CD 602 in a first axis (corresponding to the x axis in FIG. 6) and a second CD 604 in a second axis (corresponding to the y axis in FIG. 6). Note that the CD ratio of a circle is 1, while the CD ratio of an ellipse is not 1.

With reference to FIG. 7, the results of a simulation of an azimuthal scan of an elliptical contact hole array are depicted. The simulation depicted in FIG. 7 assumed a contact hole array having a photoresist on silicon structure having a pitch x, y of 400 nm, the photoresist having a thickness of 200 nm, the holes having an intended diameter of 200 nm, an angle of incidence of 65°, light having a wavelength of 500 nm, and a polarization angle P of 90°.

FIG. 7 depicts two signal measurements, in this example angle ψ, over a range of φ from 0° to 180°. As depicted in FIG. 7, the signal measures are for a CD ratio of 0.66 and 0.81. As also depicted in FIG. 7, the signal measurements, and more particularly the cross polarization terms of the signal measurements, are zero at φ of 0°, 90°, and 180°, but no longer zero at 45° and 135°.

Thus, in the present exemplary embodiment, the signal measurements at φ of 45°, 135°, 225°, or 315° can be used to detect asymmetry between first CD 602 and second CD 604 (FIG. 6) and thus an asymmetric contact hole, such as an contact hole with a shape that is an ellipse, super-ellipse, rectangle, and the like. More particularly, when the signal measurement is zero at φ of 45°, 135°, 225°, or 315°, the first CD 602 and second CD 604 are symmetric, the CD ratio is 1, and the hole is circular or symmetric. However, when the signal is not zero at φ of 45°, 135°, 225°, or 315°, the first CD 602 and second CD 604 are asymmetric, the CD ratio is not 1, and the hole has an asymmetric shape. Additionally, the amount of the asymmetry between first CD 602 and second CD 604, and thus the amount of the asymmetry of the shape of the hole, can be determined by the amount the signal deviates from zero at φ of 45°, 135°, 225°, or 315°, where the amount of the asymmetry increases as the amount the signal deviates from zero.

In addition to an azimuthal scan, a spectral scan at a particular azimuth angle can be used for characterization. For example, with reference to FIG. 8, a spectral scan at φ of 27° is shown. In this example, φ of 27° was selected because of the strong signal at φ of 27° in FIG. 7.

As described above, elliptical contact holes may be formed due to lens aberrations. Thus, in one exemplary application, the lens used in lithography can be tested/qualified by using circular contact holes on a mask, transferring the contact holes to a wafer using the mask, then determining if the contact holes formed on the wafer are circular or elliptical.

5. Rotation of Pattern Shape

With reference to FIG. 9, aberrations in the lithographic process can produce rotation of the structure formed on the semiconductor wafer. More particularly, as depicted in FIG. 9, when forming circular contact holes, in addition to the contact holes being formed as elliptical holes, actual axes 902 of a hole may be rotated by a rotation angle α compared to intended axes 904.

Thus, in one exemplary application, the signal measurements obtained during an azimuthal scan are used to detect rotation of the structure. More particularly, when the structure is rotated (e.g., in FIG. 9, when actual axes 902 is rotated from intended axes 904), the signal measurements, and more particularly the cross polarization terms of the signal measurements, are no longer zero at φ of 0, 90°, 180°, or 270°. While the signal measurements are no longer zero, there are still minima (slightly shifted in angle) at φ of 0, 90°, 180°, or 270°. Additionally, the asymmetry of the signal measurements increases with increasing rotation angle. Thus, the existence, amount, and direction of the rotation can be determined based on the asymmetry of the signal measurements.

In one exemplary embodiment, a spectrum is obtained at two azimuth angles that are symmetric about φ of 0, 90°, 180°, or 270°. A difference signal ($S_A$) is determined as the difference between the two spectra at the two azimuth angles (i.e., $S_A = S_1 - S_2$). The difference signal is zero for no rotation (i.e., α=0), but increases as the amount of rotation increases, with the maximum at α=45°. The sign of the difference signal ($S_A$) indicates the direction of the rotation.

Additionally, in the present exemplary embodiment, the spectrum at the two azimuth angles obtained to determine rotation can also be used to determine the CD ratio. An average signal ($S_{avg}$) is determined as the average between the two spectra at the two azimuth angles (i.e., $S_{avg} = (S_1 + S_2)/2$). The average signal for a rotated elliptical hole is approximately the same as the average signal for an elliptical hole that is not rotated. Thus, a separate azimuthal scan is not needed to determine the CD ratio.

With reference to FIG. 10, the results of a simulation of an azimuthal scan of a rotated elliptical contact hole array is depicted. The simulation depicted in FIG. 10 assumed a contact hole array having a photoresist on silicon structure having a pitch x, y of 400 nm, the photoresist having a thickness of 200 nm, the holes having an intended diameter of 200 nm, an angle of incidence of 65°, light having a wavelength of 500 nm, and a polarization angle P of 90°.

FIG. 10 depicts three signal measurements, in this example angle ψ, over a range of φ from −15° to +15°. In FIG. 10, signal measurements 1002, 1004, and 1006 correspond to α of 0°, 10°, and 45°, respectively. Note that signal measurement 1002 is zero at 0°, but signal measurements 1004 and 1006 are not zero at 0°.

With reference to FIG. 11, a spectral scan is depicted at φ of −8° and +8° at a rotation angle of 0° and 10°. With reference to FIG. 12, a spectral scan is depicted of a difference signal at φ of −8° and +8° at a rotation angle of −10°, +10°, and +45°. Note that the spectrum for a rotation angle of +10° is readily distinguishable from the spectrum for a rotation angle of +45°. Additionally, note that the spectrum for a rotation angle of +10° is readily distinguishable from the spectrum for a rotation angle of −10°. Thus, the difference signal can be used to determine the amount of rotation and the direction of rotation.

With reference to FIG. 13, a spectral scan is depicted of an average signal at φ of −8° and +8° at a rotation angle of 0° and +10°. Note that the spectrum for a rotation angle of 0° is nearly identical to the spectrum for a rotation angle of +10°, which confirms that the average signal for a rotated elliptical hole is the same as the average signal for an elliptical hole that is not rotated. Thus, the average signal can be used to determine the CD ratio.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching.

We claim:

1. A method of examining a structure formed on a semiconductor wafer, the method comprising:
    directing an incident beam at the structure at an incidence angle and an azimuth angle;
    scanning the incident beam over a range of azimuth angles to obtain an azimuthal scan of the structure;
    measuring the cross polarization components of diffracted beams during the azimuthal scan; and
    determining a zero azimuth position based on the measured cross polarization components,
wherein the cross polarization components are zero at the zero azimuth position.

2. The method of claim 1, wherein the incident beam is polarized at a polarization angle of zero or 90 degrees.

3. The method of claim 1, wherein the range of azimuth angles is around the zero azimuth position.

4. The method of claim 1, further comprising:
    obtaining a measured diffraction signal using an azimuth angle to be used in optical metrology of the structure, wherein the azimuthal scan is performed before the measured diffraction signal is obtained; and
    detecting azimuthal misalignment of the measured diffraction signal to a simulated diffraction signal based on the determined zero azimuth position.

5. The method of claim 4, wherein the simulated diffraction signal was generated using an assumed zero azimuth position, and wherein azimuthal misalignment of the measured diffraction signal is detected when the determined zero azimuth position differs from the assumed zero azimuth position.

6. A method of examining a structure formed on a semiconductor wafer, wherein the structure is a contact hole array, the method comprising:
    directing an incident beam at the structure at an incidence angle and an azimuth angle;
    scanning the incident beam over a range of azimuth angles to obtain an azimuthal scan of the structure;
    measuring the cross polarization components of diffracted beams during the azimuthal scan; and
    determining whether a contact hole in the contact hole array is asymmetric based on the measured cross polarization components.

7. The method of claim 6, wherein the contact hole is determined to be asymmetric when the cross polarization components are not zero at an azimuth angle of one or more of 45, 135, 225, and 315 degrees.

8. The method of claim 6, further comprising:
testing a lens used in lithography based on determining whether the contact hole in the contact hole array is asymmetric.

9. A method of examining a structure formed on a semiconductor wafer, the method comprising:
directing an incident beam at the structure at an incidence angle and an azimuth angle;
scanning the incident beam over a range of azimuth angles to obtain an azimuthal scan of the structure;
measuring the cross polarization components of diffracted beams during the azimuthal scan; and
determining rotation of the structure based on the measured cross polarization components.

10. The method of claim 9, wherein rotation of the structure is determined when the cross polarization terms reach a minimum but are not zero, and to cross polarization terms are not symmetric about the minimum.

11. The method of claim 10, further comprising:
obtaining a spectrum at two azimuth angles symmetric about the minimum; and
determining a difference signal based the spectrum obtained at the two azimuth angles,
wherein rotation of the structure is determined when the difference signal is not zero, and wherein a direction of the rotation is determined based on the sign of the difference signal.

12. A system for examining a three dimensional structure fanned on a semiconductor wafer, the system comprising:
a source configured to direct an incident beam at the structure at an incidence angle and an azimuth angle, wherein the incident beam is configured to be scanned over a range of azimuth angles to obtain an azimuthal scan of the structure;
a detector configured to measure the cross polarization components of diffracted beams during the azimuthal scan; and
a processor configured to determine a zero azimuth position based on the measured cross polarization components, wherein the cross polarization components are zero at the zero azimuth position.

13. The system of claim 12, wherein the incident beam is polarized at a polarization angle of zero or 90 degrees.

14. The system of claim 12, wherein the range of azimuth angles is around the zero azimuth position.

15. The system of claim 12, a wherein a measured diffraction signal is obtained using an azimuth angle to be used in optical metrology of the stricture, wherein the azimuthal scan is performed before the measured diffraction signal is obtained, and wherein azimuthal misalignment of the measured diffraction signal to a simulated diffraction signal is detected based on the determined zero azimuth position.

16. The system of claim 15, wherein the simulated diffraction signal was generated using an assumed zero azimuth position, and wherein azimuthal misalignment of the measured diffraction signal is detected when the determined zero azimuth position differs from the assumed zero azimuth position.

17. A system for examining a three dimensional structure formed on a semiconductor wafer, wherein the three dimensional structure is a contact hole array, the system comprising:
a source configured to direct an indent beam at the structure at an incidence angle and an azimuth angle, wherein the incident beam is configured to be scanned over a range of azimuth angles to obtain an azimuthal scan of the structure;
a detector configured to measure the cross polarization components of diffracted beams during the azimuthal scan; and
a processor configured to determine whether a contact hole in the contact hole array is asymmetric based on the measured cross polarization components.

18. The system of claim 17, wherein the contact hole is determined to be asymmetric when the cross polarization components are not zero at an azimuth angle of one or more of 45, 135, 225, and 315 degrees.

19. The system of claim 17, wherein a lens used in lithography is tested based on determining whether the contact hole in the contact hole array is asymmetric.

20. A system for examining a three dimensional structure formed on a semiconductor wafer, the system comprising:
a source configured to direct an incident beam at the structure at an incidence angle and an azimuth angle, wherein the incident beam is configured to be scanned over a range of azimuth angles to obtain azimuthal scan of the structure;
a detector configured to measure the cross polarization components of diffracted beams during the azimuthal scan; and
a processor configured to determine rotation of the structure based on the measured cross polarization components.

21. The system of claim 20, wherein rotation of the structure is determined when to cross polarization terms reach a minimum but are not zero, and to cross polarization terms are not symmetric about the minimum.

22. The system of claim 21, wherein a spectrum at two azimuth angles symmetric about the minimum is obtained, and wherein a difference signal is determined based the spectrum obtained at the two azimuth angles, wherein rotation of the structure is determined when the difference signal is not zero, and wherein a direction of the rotation is determined based on the sign of the difference signal.

23. A method of examining a structure formed on a semiconductor wafer, the method comprising:
scanning an incident beam over a range of azimuth angles to obtain an azimuthal scan of the structure;
measuring the cross polarization components of diffracted beams during the azimuthal scan; and
based on the measured cross polarization components, determining one or more of conditions including:
a) a zeroth azimuth position, wherein the cross polarization components are zero at the zero azimuth position;
b) symmetry of a contact hole in a contact bole array; and
c) rotation of the structure.

* * * * *